US012703852B2

(12) United States Patent
Kaneko et al.

(10) Patent No.: US 12,703,852 B2
(45) Date of Patent: Aug. 11, 2026

(54) HEMATOPOIETIC PROGENITOR CELL MARKER

(71) Applicants: Kyoto University, Kyoto (JP); Takeda Pharmaceutical Company Limited, Osaka (JP)

(72) Inventors: Shin Kaneko, Kyoto (JP); Shoichi Iriguchi, Kyoto (JP); Yuta Mishima, Kyoto (JP); Yoshiaki Kassai, Kanagawa (JP); Akira Hayashi, Kanagawa (JP); Suguru Arima, Kanagawa (JP)

(73) Assignees: KYOTO UNIVERSITY, Kyoto (JP); TAKEDA PHARMACEUTICAL COMPANY LIMITED, Osaka (JP)

( * ) Notice: Subject to any disclaimer, the term of this patent is extended or adjusted under 35 U.S.C. 154(b) by 914 days.

(21) Appl. No.: 16/607,967

(22) PCT Filed: Apr. 25, 2018

(86) PCT No.: PCT/JP2018/016864
§ 371 (c)(1),
(2) Date: Oct. 24, 2019

(87) PCT Pub. No.: WO2018/199186
PCT Pub. Date: Nov. 1, 2018

(65) Prior Publication Data

US 2021/0102167 A1 Apr. 8, 2021

(30) Foreign Application Priority Data

Apr. 26, 2017 (JP) ................................ 2017-087723

(51) Int. Cl.
*C12N 5/0783* (2010.01)
*C12N 5/074* (2010.01)
*G01N 33/569* (2006.01)

(52) U.S. Cl.
CPC ......... *C12N 5/0638* (2013.01); *C12N 5/0636* (2013.01); *C12N 5/0696* (2013.01); *G01N 33/56966* (2013.01); *C12N 2501/505* (2013.01); *C12N 2506/11* (2013.01)

(58) Field of Classification Search
None
See application file for complete search history.

(56) References Cited

U.S. PATENT DOCUMENTS

2007/0072295 A1 3/2007 Slukvin et al.
2012/0252060 A1* 10/2012 Dick .................... C12N 5/0647 435/372

FOREIGN PATENT DOCUMENTS

JP 2014-533494 A 12/2014
WO 2011041912 A1 4/2011
WO WO-2013075222 A1 * 5/2013 ................ A61P 7/06
WO WO-2015163185 A1 * 10/2015
WO WO-2016076415 A1 * 5/2016 ............ A61K 35/14
WO 2017/078807 A1 5/2017
WO 2017221975 A1 12/2017

OTHER PUBLICATIONS

Timmermans et al The Journal of Immunology, 182, 11, 6879-6888 (Year: 2009).*
Yu et al The Journal of Experimental Medicine • vol. 197, No. 4, 475-487 (Year: 2003).*
Vodyanik et al Blood, 2004, 104(11), 3216, pp. 1-2 (Year: 2004).*
Sonoda et al WO/2015/163185, English translation , pp. 1-17 (Year: 2015).*
Majumdar et al (J. Biomed Sci, 10, 228-241 (Year: 2003).*
Rojewski et al Transfus Med Hemother ;35:168-184 (Year: 2008).*
Vizcardo et al., Cell Stem Cell, 12:31-36 (Year: 2013).*
Ramshaw (Experimental Hematology 29 981-992 (Year: 2001).*
Sinka et al Blood, 119(16, 3712-3723 (Year: 2012).*
Zambidis Blood, 112, 3601-3614 (Year: 2008).*
Sgambato Stem Cells Translation Medicine 4, 878-886 (Year: 2015).*
Waegemans et al The Journal of Immunology, 193: 5997-6004 (Year: 2014).*
Silberstein Cell Stem Cell ;19(4):530-543 (Year: 2016).*
Wein et al Stem Cell Research 4, 129-139 (Year: 2010).*
Kawai et al Mol Ther . ;29(10):3027-304 (Year: 2021).*
Choi, K.D. et al., "Hematopoietic and Endothelial Differentiation of Human Induced Pluripotent Stem Cells", Stem Cells, 27:559-567 (2009).
Kennedy, M. et al., "T Lymphocyte Potential Marks the Emergence of Definitive Hematopoietic Progenitors in Human Pluripotent Stem Cell Differentiation Cultures", Cell Reports, 2:1722-1735 (2012).
Liu, S. et al., "Progress and challenges in generating functional hematopoietic stem/progenitor cells from human pluripotent stem cells", Cytotherapy, 17:344-358 (2015).
Timmermans et al., "Generation of T Cells from Human Embryonic Stem Cell-Derived Hematopoietic Zones," The Journal of Immunology, 182:11, pp. 6879-6888, 2009.
International Search Report from corresponding PCT Application No. PCT/JP2018/016864 dated Aug. 7, 2018.

(Continued)

*Primary Examiner* — Anoop K Singh
(74) *Attorney, Agent, or Firm* — McCarter & English, LLP; Yu Lu

(57) ABSTRACT

Provided is a method for producing a CD4/CD8 double positive cell, including the following steps:

step 1: separating, from a cell population containing a hematopoietic progenitor cell, a cell expressing one or more kinds of molecules selected from the first group consisting of CD24, CD62L, CD90, CD143, CD263, Notch3, CD32, CD39, CD49a, CD164, CD317, CD200, CD218a, CD7, CD144, CD56, CD226, CD262 and CD325, and/or a cell not expressing one or more kinds of molecules selected from the second group consisting of CD49f, CD51, CD102, CD42b, CD61, CD62P, CD69, CD102 and CD156c, and step 2: differentiating the cell separated in step 1 into a CD4/CD8 double positive cell.

3 Claims, No Drawings

(56) References Cited

OTHER PUBLICATIONS

Giesert, C. et al., (Jun. 1, 2001) "The Monocolonal Antibody W7C5 Defines a Novel Surface Antigen on Hematopoietic Stem Cells", Annals New York Academy of Sciences, 938(1):175-183.
Huijskens, M.J.A.J. et al., (Dec. 2014) "Technical Advance: Ascorbic acid induces development of double-positive T cells from human hematopoietic stem cells in the absence of stromal cells", Journal of Leukocyte Biology, 96 (6):1165-1175.
Schmitt, T.M. et al., (Dec. 1, 2002) "Induction of T Cell Development from Hematopoietic Progenitor Cells by Delta-like-1 in Vitro", Immunity, 17(6):749-756.
La Motte-Mohs, R.N. et al., (Feb. 15, 2005) "Induction of T-cell development from human cord blood hematopoietic stem cells by Delta-like 1 in vitro", Blood, 105(4):1431-1439.
Supplementary European Search Report corresponding to European Patent Application No. 18791069.0, dated Jan. 14, 2021 (7 pages).
Notta et al., Isolation of Single Human Hematopoietic Stem Cells Capable of Long-Term Multilineage Engraftment. Science. Jul. 8, 2011;333(6039):218-21.

* cited by examiner

HEMATOPOIETIC PROGENITOR CELL MARKER

CROSS REFERENCE TO RELATED APPLICATION

The present application is a National Stage Entry of the International Patent Application No. PCT/JP2018/016864 filed Apr. 25, 2018, which also claims the benefit of priority of the Japanese Patent Application No. 2017-087723 filed Apr. 26, 2017. The entire contents of each of which are incorporated herein for all purposes by this reference.

TECHNICAL FIELD

The present invention relates to a method of producing a CD8 positive cell by using one or more kinds of hematopoietic progenitor cell markers (HPC markers) and a cell population expressing the one or more kinds of HPC markers and the like.

BACKGROUND OF THE INVENTION

T cells play a central role in immune systems against foreign pathogens such as bacteria, viruses and the like and abnormal cells such as cancer cells and the like. Particularly, cytotoxic T lymphocyte (CTL) recognizes, via the T cell receptor (TCR) present on its cell surface, antigenic peptides derived from viruses, tumors, etc. and presented together with class 1 major histocompatible antigen of antigen-presenting cells, and specifically exerts cytotoxic activity against cells presenting said antigenic peptide as a foreign substance.

Most CTLs are CD8 single positive (SP) cells. The above-mentioned CD8SP cell is known to be differentiated in the thymus from immature cells not expressing TCR and without CD4 or CD8 (CD4/CD8 double negative (double negative is sometimes indicated as DN in the present specification) cells) via a cell expressing CD8 and CD4 (CD4/CD8 double positive (double positive is sometimes indicated as DP in the present specification) cells).

As mentioned above, since T cell plays a central role in the immune system, if T cell can be supplemented or regenerated, it becomes an extremely effective means for preventing or treating diseases such as tumor, infection, autoimmune disorder and the like. Therefore, attempts have been made to obtain hematopoietic progenitor cells and T cell line cells by a method for inducing hematopoietic progenitor cell (sometimes to be referred to as HPC in the present specification) from iPS cells, a method for further inducing CD4/CD8DP cells and the like. For example, non-patent document 1 describes that CD34/CD43DP cells can be induced by coculturing iPS cells with feeder cells (specifically, OP9 cell). Patent document 1 and non-patent document 2 describe a method for separating HPC from a cell population containing HPC induced from human pluripotent stem cell, with the expression of CD43 and CD34, CD31 or CD144 as an index, a method for differentiating separated cells into T cell line cells, and describe that, when differentiating pluripotent stem cells into HPC, the properties of blood-lineage cells induced vary depending on whether or not Activin/Nodal acts in the early stage of induction. Patent document 2 describes a method for producing CD4/CD8DP under feeder-free conditions. Also, non-patent document 3 teaches various methods for inducing hematopoietic cells including hematopoietic progenitor cells from human pluripotent stem cells, and recites low induction efficiency as a reason why clinical use of hematological cells induced in vitro does not proceed.

DOCUMENT LIST

Patent Document patent document 1: WO 2013/075222 patent document 2: WO 2017/221975

Non-Patent Documents non-patent document 1: Choi K. D. et al., Stem Cells, 27 (2009); 559-567 non-patent document 2: Kennedy M. et al., Cell Reports, 2 (2012); 1722-1735 non-patent document 3: Liu S. et al., Cytotherapy, 17 (2015); 344-358

SUMMARY OF THE INVENTION

Problems to be Solved by the Invention

The present invention aims to obtain more T cell line cells (e.g., CD8 positive cell (e.g., CD4/CD8DP cell, CD8SP cell)) and/or obtain them at higher concentrations (i.e., provision of a production method of the cell) to stably provide a cell therapy. In addition, the present invention aims to provide a cell population containing hematopoietic progenitor cells to solve the above-mentioned objects.

Means of Solving the Problems

To develop a production method of CD4/CD8DP cells that solves the above-mentioned problem, the present inventors identified markers expressed on the surface of HPC (HPC markers). Furthermore, they have found that HPC separated from a cell population containing HPC by using one or more kind of the markers shows high differentiation efficiency into CD8 positive cells (e.g., CD4/CD8DP cells) and high proliferation potency as well, that is, more CD8 positive cells (e.g., CD4/CD8DP cells) can be obtained and/or they can be obtained at higher concentrations within the cell population by using the one or more kinds of HPC markers. Furthermore, they have found that the production method of the present invention shows less variation in the yield and can stably provide CD8 positive cells (e.g., CD4/CD8DP cells), which resulted in the completion of the present invention.

Therefore, the present invention provides the following.

[1] A method for producing CD4/CD8 double positive cells, the method comprising the following steps:

step 1: separating from a cell population comprising hematopoietic progenitor cells, cells expressing one or more kinds of molecules selected from the first group consisting of CD24, CD62L, CD90, CD143, CD263, Notch3, CD32, CD39, CD49a, CD164, CD317, CD200, CD218a, CD7, CD144, CD56, CD226, CD262 and CD325, and/or a cell not expressing one or more kinds of molecules selected from the second group consisting of CD49f, CD51, CD102, CD42b, CD61, CD62P, CD69, CD102 and CD156c, and step 2: differentiating the cells separated in step 1 into CD4/CD8 double positive cells.

[2] The method of [1], wherein the cells selected in the aforementioned step 1 do not express CD235a or CD14 but express CD45, CD34 and CD43.

[3] The method of [1] or [2], wherein the aforementioned step 1 comprises separating, from a cell population comprising hematopoietic progenitor cells, cells expressing one or more kinds of molecules selected from the first group consisting of CD24, CD62L, CD90, CD143, CD263, Notch3, CD32, CD39, CD49a, CD164, CD317, CD200, CD218a, CD7, CD144, CD56, CD226, CD262 and CD325.

[4] The method of [3], wherein the first group in the aforementioned step 1 consisting of CD24, CD62L, CD90, CD143, CD263, Notch3, CD200, CD218a, CD7 and CD144.

[5] The method of [1] or [2], wherein the aforementioned step 1 comprises separating, from a cell population comprising hematopoietic progenitor cells, cells not expressing one or more kinds of molecules selected from the second group consisting of CD49f, CD51, CD102, CD42b, CD61, CD62P, CD69, CD102 and CD156c.

[6] The method of [5], wherein the second group in the aforementioned step 1 consisting of CD49f, CD51 and CD102.

[7] The method of any of [1] to [6], wherein the cell population comprising hematopoietic progenitor cells in the aforementioned step 1 is obtained by inducing differentiation of pluripotent stem cells.

[8] The method of [7], wherein the aforementioned pluripotent stem cells are human induced pluripotent stem cells.

[9-1] A method for producing CD8 single positive cells, comprising a step of inducing CD4/CD8 double positive cells obtained by the method of any of [1] to [8] into CD8 single positive cells.

[9-2] The method of [9-1] wherein the aforementioned step of inducing for example comprises culturing the CD4/CD8 double positive cells in the presence of an adrenocortical hormone agent, an antibody, and/or a cytokine, preferably wherein the adrenocortical hormone agent is dexamethasone, and/or the antibody is an anti-CD3 antibody, and/or the cytokine is IL-2.

[10] The method of [9-1] or [9-2], wherein the aforementioned CD8 single positive cells are cytotoxic T lymphocytes.

[11] A cell population obtained by separating, from a cell population comprising hematopoietic progenitor cells, cells expressing one or more kinds of molecules selected from the first group consisting of CD24, CD62L, CD90, CD143, CD263, Notch3, CD32, CD39, CD49a, CD164, CD317, CD200, CD218a, CD7, CD144, CD56, CD226, CD262 and CD325, and/or cells not expressing one or more kinds of molecules selected from the second group consisting of CD49f, CD51, CD102, CD42b, CD61, CD62P, CD69, CD102 and CD156c.

[12] The cell population of [11], wherein the separated cell does not express CD235a or CD14 and express CD45, CD34 and CD43.

[13] The cell population of [11] or [12], wherein the aforementioned cell population comprising hematopoietic progenitor cells is obtained by inducing differentiation of pluripotent stem cells.

[14] The cell population of [13], wherein the aforementioned pluripotent stem cells are human-induced pluripotent stem cells.

[15] A cell population comprising hematopoietic progenitor cells expressing one or more kinds of molecules selected from the first group consisting of CD24, CD62L, CD90, CD143, CD263, Notch3, CD32, CD39, CD49a, CD164, CD317, CD200, CD218a, CD7, CD144, CD56, CD226, CD262 and CD325, and/or hematopoietic progenitor cells not expressing one or more kinds of molecules selected from the second group consisting of CD49f, CD51, CD102, CD42b, CD61, CD62P, CD69, CD102 and CD156c, at a ratio of [number of the hematopoietic progenitor cells/total number of cells in the cell population] not less than 40%.

[16] The cell population of [15], wherein the ratio is of the hematopoietic progenitor cells further expressing one or more kinds of molecules selected from the first group consisting of CD24, CD62L, CD90, CD143, CD263, Notch3, CD200, CD218a, CD7 and CD144.

[17] The cell population of [15], wherein the ratio is of the hematopoietic progenitor cells further not expressing one or more kinds of molecules selected from the second group consisting of CD49f, CD51 and CD102.

[18] A reagent for separating hematopoietic progenitor cells, the reagent comprising an antibody to each of one or more kinds of molecules selected from the group consisting of CD24, CD62L, CD90, CD143, CD263, Notch3, CD32, CD39, CD49a, CD164, CD317, CD200, CD218a, CD7, CD144, CD56, CD226, CD262, CD325, CD49f, CD51, CD102, CD42b, CD61, CD62P, CD69, CD102 and CD156c.

[19] The reagent of [18] further comprising one or more kinds of antibodies to CD235a, CD14, CD45, CD34 and/or CD43.

[20] A method of detecting a protein on the surface of a hematopoietic progenitor cell, the method comprising contacting the hematopoietic progenitor cell with a reagent that specifically binds to CD24, CD62L, CD90, CD143, CD263, Notch3, CD32, CD39, CD49a, CD164, CD317, CD200, CD218a, CD7, CD144, CD56, CD226, CD262, CD325, CD49f, CD51, CD102, CD42b, CD61, CD62P, CD69, CD102, CD109 or CD156c.

[21] The method according to [20], wherein the reagent comprises an antibody or a fragment thereof.

[22] The method according to [20] or [21], wherein the reagent further comprises a fluorophore.

[23] The method according to any one of [20] to [22], further comprising contacting the hematopoietic progenitor cell with a reagent that specifically binds to CD34, CD43, CD14, or CD235a.

[24] A method of detecting multiple proteins on the surface of a hematopoietic progenitor cell, the method comprising contacting the hematopoietic progenitor cell with a reagent that specifically binds to each of the multiple proteins, wherein the multiple proteins comprise any combination of two or more kinds of proteins selected from the group consisting of 2, 3, 4, 5, 6, 7, 8, 9, 10, 11, 12, 13, 14, 15, 16, 17, 18, 19, 20, 21, 22, 23, 24, 25, 26, 27, 28 or all 29 of: CD24, CD62L, CD90, CD143, CD263, Notch3, CD32, CD39, CD49a, CD164, CD317, CD200, CD218a, CD7, CD144, CD56, CD226, CD262, CD325, CD49f, CD51, CD102, CD42b, CD61, CD62P, CD69, CD102, CD109, and CD156c.

[25] A method of selecting a hematopoietic progenitor cell from a cell population comprising hematopoietic progenitor cells, the method comprising detecting the presence or absence of one or more kinds of proteins on the surface of the cell according to the method of any one of [20]-[24], and selecting the cell if (i) one or more kinds of the following proteins are detected on the surface of the cell: CD24, CD62L, CD90, CD143, CD263, Notch3, CD32, CD39, CD49a, CD164, CD317, CD200, CD218a, CD7, CD144, CD56, CD226, CD262, and CD325, and/or if (ii) one or more kinds of the following proteins are not detected on the surface of the cell: CD49f, CD51, CD102, CD42b, CD61, CD62P, CD69, CD102, CD109 and CD156c.

[26] The method according to [25], wherein the cell is selected if one or more kinds of the following proteins are detected on the surface of the cell: CD24, CD62L, CD90, CD143, CD263, Notch3, CD200, CD218a, CD7, and CD144.

[27] The method according to [25] or [26], wherein the cell is selected if one or more kinds of the following proteins is not detected on the surface of the cell: CD49f, CD51, and CD102.

[28] A method of selecting a hematopoietic progenitor cell from a cell population comprising hematopoietic progenitor cells, the method comprising detecting the presence or absence of one or more kinds of proteins on the surface of the cell according to the method of any one of [20]-[24], and selecting the cell if (i) CD45, CD34 and/or CD43 and one or more kinds of the following proteins are detected on the surface of the cell: CD24, CD62L, CD90, CD143, CD263, Notch3, CD32, CD39, CD49a, CD164, CD317, CD200, CD218a, CD7, CD144, CD56, CD226, CD262, and CD325, and/or if (ii) CD14 and/or CD235a is not detected on the surface of the cell, and one or more kinds of the following proteins are also not detected on the surface of the cell: CD49f, CD51, CD102, CD42b, CD61, CD62P, CD69, CD102, CD109 and CD156c.

Effect of the Invention

The production method of the present invention using one kind of HPC markers can provide more CD8 positive cells (e.g., CD4/CD8DP cell, CD8SP cell) and/or generate CD8 positive cells at a higher concentration. Furthermore, the production method of the present invention can stably provide CD8 positive cells (e.g., CD4/CD8DP cells, CD8SP cells) with less variation in the yield. The production method of the present invention thus provides an improved method for separating hematopoietic progenitor cells from a population of cells. This provides an improved cellular source for generation of CD8 positive cells. This novel production method is based on the inventors' surprising and unexpected finding that certain HPC positive markers and HPC negative markers can be used to greatly improve the quality and/or quantity of HPC-derived CD8 positive cell populations. This advantageous source of CD8 positive cells of the present invention provides improved CD8 positive cell populations for clinical applications (e.g., in cell therapy, diagnostic purposes, and in vitro applications).

DETAILED DESCRIPTION OF THE INVENTION

The present invention provides a method for producing CD8 positive cells (e.g., CD4/CD8DP cell), including (step 1) separating cells expressing one or more kinds of hematopoietic progenitor cell markers (sometimes to be abbreviated as "HPC marker" in the present specification") and/or a cell not expressing one or more kinds of HPC markers from a cell population containing a hematopoietic progenitor cell, and (step 2) differentiating the cells separated in step 1 into a CD8 positive cells (e.g., CD4/CD8 double positive cell (sometimes to be abbreviated as "CD4/CD8DP cell" in the present specification) (hereinafter to be abbreviated as "the production method of the present invention") and the like.

In the present invention, the "CD8 positive cell" means a cell expressing CD8, and examples thereof include CD4/CD8DP cell and CD8 single positive cell (sometimes to be abbreviated as "CD8SP cell" in the present specification). In the present invention, the "CD4/CD8DP cell" means a T cell simultaneously expressing CD4 and CD8, and the "CD8SP cell" means a T cell not expressing CD4 but expressing CD8. Examples of the CD8SP cell include cytotoxic T lymphocyte and progenitor cell thereof. In the present invention, moreover, "T cell" means, for example, a cell expressing an antigen receptor called a T cell receptor (TCR) on its surface, and a progenitor cell thereof (e.g., pro-T cell not expressing TCR (TCRαβ), pre-T cell in which TCRβ and pre-TCRα are associated).

In the present invention, the "hematopoietic progenitor cell" means a CD34 positive cell, preferably a CD34/CD43DP cell. The derivation of the hematopoietic progenitor cell to be used in the present invention is not limited and may be, for example, a hematopoietic progenitor cell induced in vitro (e.g., a hematopoietic progenitor cell obtained by inducing differentiation of pluripotent stem cell) by a known method (e.g., methods described in patent documents 1, 2, non-patent documents 1-3), or a hematopoietic progenitor cell isolated from a biological tissue by a known method.

Examples of the pluripotent stem cell include embryonic stem cell (ES cell), induced pluripotent stem cell (iPS cell), embryonic carcinoma cell (EC cell) and embryonic germ cell (EG cell), preferably iPS cell (more preferably human iPS cell). When the above-mentioned pluripotent stem cell is ES cell or any cell derived from human embryo, the cell may be produced by destroying an embryo or produced without destroying embryo, with preference given to a cell produced without destroying embryo.

The above-mentioned iPS cell is an artificial stem cell derived from a somatic cell having characteristics substantially equal to those of ES cell, for example, pluripotency and proliferation potency by self-replication, and can be produced by introducing particular reprogramming factors in the form of DNA or protein into a somatic cell (e.g., Takahashi K. and Yamanaka S. (2006) Cell, 126; 663-676: Takahashi K. et al. (2007) Cell, 131; 861-872: Yu J. et al. (2007) Science, 318; 1917-1920: Nakagawa M. et al. (2008) Nat. Biotechnol. 26; 101-106). When an iPS cell is used, it may be produced from a somatic cell by a method known per se or iPS cell already established and stocked may also be used. While the somatic cell from which iPS cell to be used in the present invention is derived is not limited, it is preferably a cell derived from peripheral blood or cord blood. The animal from which pluripotent stem cell is derived is not limited and, for example, mammals such as mouse, rat, hamster, guinea pig, dog, monkey, orangutan, chimpanzee, human and the like can be mentioned, with preference given to human.

A hematopoietic progenitor cell can be produced by subjecting the aforementioned pluripotent stem cell to a method known per se. When the aforementioned pluripotent stem cell is an iPS cell, a hematopoietic progenitor cell can be produced by the method described in, for example, WO 2017/221975.

The aforementioned biological tissue is not particularly limited as long as it contains hematopoietic progenitor cells. Examples thereof include peripheral blood, lymph node, bone marrow, thymus, spleen and cord blood. Of these, peripheral blood and cord blood are preferable since they show low invasiveness in animals and preparation thereof is easy.

The hematopoietic progenitor cell and pluripotent stem cell to be used in the present invention are preferably cells meeting the GMP (Good Manufacturing Practice) standard from the zo aspect of application to treatments.

In the present invention, the "HPC marker" means any molecule from CD24, CD62L, CD90, CD143, CD263, Notch3, CD32, CD39, CD49a, CD164, CD317, CD200, CD218a, CD7, CD144, CD56, CD226, CD262 and CD325, which are molecules possibly expressed on the surface of hematopoietic progenitor cell (in the specification, these markers are sometimes referred to as "HPC positive marker(s)", "positive HPC selection marker(s)", or "positive HPC marker(s)"), or any molecule from CD49f, CD51, CD102, CD42b, CD61, CD62P, CD69, CD102 and CD156c, which are molecules not generally expressed on the surface of hematopoietic progenitor cell (in the specification, these markers are sometimes referred to as "HPC negative marker(s)", "negative HPC selection marker(s)", or "negative HPC marker(s)") (In the present description, HPC positive marker and HPC negative marker are sometimes to be collectively referred to as "the HPC marker(s) of the present invention"). Of the HPC positive markers of the present invention, CD24, CD62L, CD90, CD143, CD263, Notch3, CD200, CD218a, CD200, CD7 or CD144 is preferable, and CD90, CD143, CD218a or CD200 is more preferable. In another embodiment, CD24, CD62L, CD90, CD143, CD263, Notch3, CD32, CD39, CD49a, CD164, CD317, CD200 or CD218a is preferable, and CD24, CD62L, CD90, CD143, CD263, Notch3, CD200 or CD218a is more preferable. In the present invention, moreover, a cell expressing the aforementioned HPC positive marker is sometimes called an HPC marker positive cell (or HPC marker positive cell) and, for example, a cell expressing CD24 molecule is sometimes called a CD24 positive cell. Of the HPC negative markers of the present invention, CD49f, CD51 or CD102 is preferable. In the present invention, a cell that does not express the aforementioned HPC negative markers is sometimes referred to as an HPC marker negative cell.

In an exemplary embodiment, the CD8 positive cells, preferably CD4/CD8 double positive cells, are produced by separating, from a cell population comprising hematopoietic progenitor cells, cells (a) expressing CD34 and CD43, and (b) expressing either CD62L, CD24, CD90, CD143, CD218a, CD263, or Notch3, and (c) not expressing CD235a or CD14.

In an exemplary embodiment, the CD8 positive cells, preferably CD4/CD8 double positive cells, are produced by separating, from a cell population comprising hematopoietic progenitor cells, cells expressing (a) CD34 and CD43, and (b) expressing either CD90, CD143, CD200, CD218a, or CD263, and (c) not expressing CD235a or CD14.

In an exemplary embodiment, the CD8 positive cells, preferably CD4/CD8 double positive cells, are produced by separating, from a cell population comprising hematopoietic progenitor cells, cells expressing (a) CD34 and CD43, and (b) expressing either CD7, CD144, CD56, CD226, CD262, or CD325 and (c) not expressing CD235a or CD14.

In an exemplary embodiment, the CD8 positive cells, preferably CD4/CD8 double positive cells, are produced by separating, from a cell population comprising hematopoietic progenitor cells, cells expressing (a) CD34 and CD43, and (b) not expressing either CD49f, CD51, CD426, CD61, CD62P, CD69, or CD156c and (c) not expressing CD235a or CD14.

In the present invention, "expressing" means that the expression can be detected by the method used for separating cells, and "not expressing" means that the detection is not possible with the detection sensitivity of the method used for separating cells. As the method used for separating cells, a method using the below-mentioned flow cytometry or mass cytometry, a magnetic cell separation method and the like can be mentioned.

As the cell separated by the aforementioned step 1, a cell expressing one or more kinds of HPC positive markers, a cell not expressing one or more kinds of HPC negative markers can be mentioned. In one embodiment of the present invention, the cells separated by the aforementioned step 1 are cells expressing CD34 and/or CD43 in addition to one or more kinds of HPC positive markers of the present invention, and/or are cells not expressing one or more kinds of HPC negative markers of the present invention and expressing CD34 and/or CD43. The cell to be separated is preferably CD235a negative, CD14 negative and/or CD45 positive. Therefore, in a preferable embodiment of the present invention, the aforementioned step 1 is performed by separating one or more kinds of cells which are CD235a negative, CD14 negative, CD45 positive, CD34 positive and CD43 positive, and positive for one or more kinds of the positive HPC marker(s) of the present invention and/or cells negative for one or more kinds of the negative HPC markers of the present invention, from a cell population containing hematopoietic progenitor cells.

In the present invention, "separating cells" encompasses an embodiment including selecting cells expressing one or more kinds of HPC positive markers and/or not expressing one or more kinds of HPC negative markers and isolating the selected cells, and an embodiment including subjecting the selected cells to a next differentiation step.

As used herein, each occurrence of terms such as "comprising" or "comprises" may optionally be substituted with "consisting of" or "consists of".

Examples of the method for separating cells expressing one or more kinds of HPC positive markers and/or not expressing one or more kinds of HPC negative markers from a cell population containing hematopoietic progenitor cells include a method using flow cytometry or mass cytometry, a magnetic cell separation method and the like, and these methods can be performed using known methods. For example, a cell expressing one or more kinds of HPC positive markers and/or a cell not expressing one or more kinds of HPC negative markers can be separated by a method including a step of contacting the cell with a substance (e.g., antibody) that specifically binds to each HPC marker. The above-mentioned substance includes one directly added with a detectable label (e.g., GFP) and one not directly added with a label. When the above-mentioned substance is one not directly added with a label, the above-mentioned separation can be performed by further using a substance added with a detectable label that directly or indirectly recognizes the substance. For example, when the above-mentioned substance is an antibody, the antibody may carry, directly or indirectly, a fluorescence dye, metal isotope or bead (e.g., magnetic bead) to thereby label an HPC marker on the cell surface. The cells can be separated based on the label. The antibody used here may be only one kind or two or more kinds of antibodies.

Examples of the method for differentiating a cell separated as a cell expressing one or more kinds of HPC positive markers and/or not expressing one or more kinds of HPC negative markers of the present invention from a cell population containing hematopoietic progenitor cells into CD8 positive cells include known methods (e.g., methods described in WO 2016/076415, Journal of Leukocyte Biology 96(2016)1165-1175, Cell Reports 2(2012) 1722-1735, WO 2017/221975).

1. Production Method of CD4/CD8DP Cells

Examples of the basal medium for cell culture to be used in step 2 of the production method of the present invention include Iscove's Modified Dulbecco's Medium (IMDM) medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, Neurobasal Medium (Life Technologies) and a mixed medium of these. The medium may or may not contain serum. Where necessary, the basal medium may also contain one or more substances from Vitamin Cs (e.g., ascorbic acid, vitamin c phosphate), albumin, insulin, transferrin, selenium, fatty acid, trace elements, 2-mercaptoethanol, thiol glycerol, lipids, amino acids, L-glutamine, non-essential amino acids, vitamins, growth factors, low-molecular-weight compounds, antibiotics, antioxidants, pyruvic acid, buffers, inorganic salts, cytokines, and the like.

The aforementioned medium preferably contains cytokine. As the cytokine, IL-7, FLT-3L, SCF, TPO and a combination of these and the like can be mentioned, and FLT-3L and IL-7 are preferable. The concentration of IL-7 in the medium is preferably 1 ng/ml-50 ng/ml (e.g., 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 30 ng/ml, 40 ng/ml, 50 ng/ml), and 5 ng/ml is particularly preferable. The concentration of FLT-3L in the medium is preferably 1 ng/ml-100 ng/ml (e.g., 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, 100 ng/ml), and 10 ng/ml is particularly preferable. Those of ordinary skill in the art can appropriately determine the concentration of other cytokines based on the culture conditions and the like. The medium preferably contains a Notch ligand (e.g., fusion protein of D111, D114, D111 or D114, and Fc). When a Notch ligand is used, it may be added to the medium, or coated on the culture container. In addition, a feeder cell expressing a Notch ligand may also be used.

In the production method of the present invention, the hematopoietic progenitor cells obtained in step 1 may be cultured by adherent culture or suspension culture. In cases of adherent culture, a coated culture vessel may be used, and the hematopoietic progenitor cells may be co-cultured with feeder cells and other cells. For application to the treatments, it is preferable feeder free. Examples of the substrate for coating a culture container include fibronectin fragment (e.g., RetroNectin), Pronectin, vitronectin, Matrigel (BD), Type I collagen, Type IV collagen, gelatin, laminin, heparan sulfuric acidproteoglycan, entactin, and a combination of these. As a feeder cell to be cocultured, for example, OP9 cell of bone marrow interstitial cell line, 10T1/2 cell of mouse mesenchymal cell line, and Tst-4 cell can be mentioned. When feeder cells are used, they are preferably appropriately replaced during the culture. The replacement of the feeder cells may be carried out by transferring the subject cells that are being cultured onto feeder cells that are preliminarily plated. The replacement is preferably performed every 2 to 5 days.

In the present invention, the culture temperature conditions for culturing the hematopoietic progenitor cells to induce CD4/CD8 DP cells are not limited. The temperature is preferably about 37° C. to about 42° C., more preferably about 37 to about 39° C. The culture period can be appropriately determined by those skilled in the art by monitoring of the number of CD4/CD8 DP cells and other cells. The number of days of the culture, which induces CD4/CD8 DP cells from the hematopoietic progenitor cells, is not limited as long as CD4/CD8 DP cells can be obtained. It is preferably not less than 10 days (e.g., 12 days, 14 days, 16 days, 18 days, 20 days or longer), and not more than 60 days is preferable. As shown in the below-mentioned Examples, in a particular embodiment, a large amount of CD4/CD8DP cell can be efficiently obtained by culturing for 21 days-28 days.

In the present invention, the obtained CD4/CD8DP cells may be isolated before use, or may be used as a cell population containing other cell type (e.g., CD8SP cell). When isolated, the cells can be isolated using CD4, CD8, CD3, CD45 molecules and the like as an index. As the isolation method, a method well known to those of ordinary skill in the art can be used and, for example, a method including labeling with an antibody to a molecule to be the index and using the aforementioned flow cytometry or mass cytometry, a magnetic cell separation method, or a purification method using an affinity column on which a desired antigen is immobilized and the like can be mentioned.

2. Production Method of CD8 Single Positive Cells

CD8SP cells can be produced by subjecting the CD4/CD8DP cells obtained by the production method of the present invention to a step for inducing differentiation into CD8SP cells (such production method of CD8SP cells is sometimes to be abbreviated as "the production method of CD8SP cells of the present invention"). The production method of CD4/CD8DP cells is as described in 1.

As the basal medium and medium to be used for the production method of CD8SP cells of the present invention, those similar to the basal medium and medium described in 1. can be mentioned.

The aforementioned medium may contain an adrenocortical hormone agent. Examples of the adrenocortical hormone agent include, for example, a glucocorticoid and a derivative thereof. Examples of the glucocorticoid include, for example, cortisone acetate, hydrocortisone, fludrocortisone acetate, prednisolone, triamcinolone, methylprednisolone, dexamethasone, betamethasone, and beclometasone dipropionate. Of these, dexamethasone is preferable. Thus, in one embodiment, the method for producing CD8 single positive cells comprises a step of inducing CD4/CD8 double positive cells into CD8 single positive cells by culturing said CD4/CD8 double positive cells in the presence of an adrenocortical hormone agent, preferably dexamethasone.

When dexamethasone is used as the adrenocortical hormone agent, its concentration in the culture medium is preferably 1 nM-100 nM (e.g., 1 nM, 5 nM, 10 nM, 20 nM, 30 nM, 40 nM, 50 nM, 60 nM, 70 nM, 80 nM, 90 nM, 100 nM), particularly preferably 10 nM.

The aforementioned medium may contain antibody (e.g., anti-CD3 antibody, anti-CD28 antibody, anti-CD2 antibody), cytokine (e.g., IL-7, IL-2, IL-15) and the like.

Anti-CD3 antibody used in the present invention is not particularly limited as long as it specifically recognizes CD3. For example, an antibody produced from OKT3 clone can be mentioned. The anti-CD3 antibody may be bonded to magnetic beads and the like or, instead of adding the aforementioned anti-CD3 antibody to the medium, stimulation may be given by incubating the T lymphocytes for a given period on a culture vessel to which the anti-CD3 antibody is bound on the surface thereof. The concentration of anti-CD3 antibody in the medium is preferably 10 ng/ml-1000 ng/ml (e.g., 10 ng/ml, 50 ng/ml, 100 ng/ml, 200 ng/ml, 300 ng/ml, 400 ng/ml, 500 ng/ml, 600 ng/ml, 700 ng/ml, 800 ng/ml, 900 ng/ml, 1000 ng/ml), particularly preferably 500 ng/ml. The concentration of other antibodies can also be appropriately determined by those of ordinary skill in the art based on the culture conditions and the like. Thus, in one embodiment, the method for producing CD8 single positive cells comprises a step of inducing CD4/CD8 double positive cells into CD8 single positive cells by culturing said CD4/CD8 double positive cells in the presence of an anti-CD3 antibody.

The concentration of IL-2 in the medium used in the present invention is preferably 10 U/ml-1000 U/ml (e.g., 10 U/ml, 20 U/ml, 30 U/ml, 40 U/ml, 50 U/ml, 60 U/ml, 70 U/ml, 80 U/ml, 90 U/ml, 100 U/ml, 500 U/ml, 1000 U/ml), particularly preferably 100 U/ml. The concentration of IL-7 or IL15 in the medium used in the present invention is preferably 1 ng/ml-100 ng/ml (e.g., 1 ng/ml, 5 ng/ml, 10 ng/ml, 20 ng/ml, 30 ng/ml, ng/ml, 50 ng/ml, 60 ng/ml, 70 ng/ml, 80 ng/ml, 90 ng/ml, 100 ng/ml), particularly preferably 10 ng/ml. Thus, in one embodiment, the method for producing CD8 single positive cells comprises a step of inducing CD4/CD8 double positive cells into CD8 single positive cells by culturing said CD4/CD8 double positive cells in the presence of a cytokine, preferably IL-2.

In the production method of CD8SP cells of the present invention, the temperature conditions for culturing the CD4/CD8DP cells are not particularly limited. The temperature is preferably about 37° C. to about 42° C., more preferably about 37 to about 39° C. The culture period may be appropriately determined by those skilled in the art by monitoring the number of CD8 positive cells and other cells. The number of days of the culture is not limited as long as CD8SP cells can be obtained. The culture period is preferably not less than 1 day, not less than 3 days, not less than 7 days, and preferably not more than 60 days.

CD8SP cells produced by the production method of the present invention is not limited to the cells obtained by differentiation from CD4/CD8DP cells (e.g., cells obtained in the above-mentioned 2.). Therefore, for example, CD8SP cells induced, without via CD4/CD8DP cells, from cells separated as a cell expressing one or more HPC positive markers and/or not expressing one or more HPC negative markers of the present invention from a cell population containing hematopoietic progenitor cells is also encompassed in the CD8SP cells produced by the production method of the present invention.

3. Cell Population Containing Hematopoietic Progenitor Cells Expressing One or More HPC Markers The present invention provides a cell population (hereinafter to be abbreviated as "the cell population of the present invention") containing, at high frequency, hematopoietic progenitor cells expressing one or more kinds of HPC positive markers and/or not expressing one or more HPC negative markers. The aforementioned cell population can be obtained by, for example, separating cells expressing one or more HPC positive markers and/or not expressing one or more HPC negative markers from a cell population containing hematopoietic progenitor cells by a separation method described above. The definition of HPC marker, specific molecules and definition of hematopoietic progenitor cell are as described above.

The cell population of the present invention is not limited as long as it shows a higher ratio of a hematopoietic progenitor cells expressing one or more kinds of HPC positive markers and/or not expressing one or more kinds of HPC negative markers (number of hematopoietic progenitor cells/total number of cells contained in cell population) than that obtained by a conventional method (e.g., method of separation using CD34 positive, CD34 positive and CD43 positive, or CD43 positive and CD34, CD31 or CD144 positive as an index). It is preferably not less than 40% (e.g., not less than 50%, not less than 60%, not less than 70%, not less than 80%, not less than 90%, 100%). The cell population of the present invention can be obtained by the method described in step 1 of the production method of the present invention. The proportion of the hematopoietic progenitor cells expressing one or more HPC positive markers and/or not expressing one or more HPC negative markers can be measured by flow cytometry.

As shown in the below-mentioned Examples, the cell population of the present invention shows high differentiation efficiency into CD4/CD8DP cells and CD8SP cells as compared to a cell population that has not undergone separation of a cell expressing one or more kinds of HPC positive markers and/or not expressing one or more kinds of HPC negative markers, and is also superior in the proliferation potency.

4. Reagent for Separating "the Cell Population of the Present Invention"

The present invention also provides a reagent for separating the cell population of the present invention (hereinafter to be abbreviated as "the reagent of the present invention"), which contains an antibody to the HPC marker of the present invention, namely, one or more kinds of markers selected from the group consisting of CD24, CD62L, CD90, CD143, CD263, Notch3, CD32, CD39, CD49a, CD164, CD317, CD200, CD218a, CD7, CD144, CD56, CD226, CD262, CD325, CD49f, CD51, CD102, CD42b, CD61, CD62P, CD69, CD102 and CD156c, preferably, CD24, CD62L, CD90, CD143, CD263, Notch3, CD200, CD218a, CD7, CD144, CD49f, CD51 and CD102. When the reagent of the present invention contains antibodies to two or more kinds of HPC marker, the reagent may be provided as a reagent kit containing each antibody in a separate reagent. The antibody to be contained in the reagent of the present invention may be provided in the form of, for example, fluorescence dye, metal isotope or bead (e.g., magnetic bead) bonded thereto, according to the separation means used in step 1 of the production method of the present invention.

The reagent of the present invention can further contain an anti-CD4 antibody and/or an anti-CD8 antibody and, where necessary, one or more kinds of antibodies to other cell surface markers (e.g., CD3, CD45, CD235a, CD14, CD45, CD34, CD43) known to express or not express in CD4/CD8DP cell and/or CD8SP cell, and can be used as a reagent for separating CD4/CD8DP cell or CD8SP cell induced to differentiate from the cell population of the present invention.

In addition, the reagent of the present invention can further contain reagents (e.g., basal medium, medium additive and the like) for inducing differentiation of hematopoietic progenitor cells into CD4/CD8DP cell and further into CD8SP cell. As the reagents, substances exemplified in the above-mentioned 1. and the above-mentioned 2. can be similarly recited.

The present invention is explained in more detail in the following by referring to Examples, which are mere exemplifications and do not limit the present invention.

EXAMPLES

Example 1 (Consideration Using TKT3V1-7 Strain)

As a cell population containing hematopoietic progenitor cells (hereinafter sometimes referred to as HPC), a non-adherent cell population obtained by differentiation of iPS cells (TKT3V1-7 strain) according to a known method (for example, the methods described in Cell Reports 2(2012) 1722-1735 and WO 2017/221975) was used. To be specific, TKT3V1-7 strain was seeded at $3\times10^5$ cells/well in a 6 well plate that underwent an ultra low adhesion treatment (Day0), and cultured for 5 days under low oxygen conditions (5% $0_2$) in EB medium (StemPro34 added with 10 μg/ml human insulin, 5.5 μg/ml human transferrin, 5 ng/ml sodium selenite, 2 mM L-glutamine, 45 mM α-monothioglycerol and 50 μg/ml ascorbic acid) supplemented with 10 ng/ml BMP4, 5 ng/ml bFGF, 15 ng/ml VEGF, 2 μM SB431542 (Day5). Successively, 50 ng/ml SCF, 30 ng/ml TPO, 10 ng/ml Flt3L were added and the cells were further cultured for 5-9 days (–Day14) to give a non-adherent cell population. The medium was exchanged every 2 or 3 days during the culture period. The above-mentioned non-adherent cell population containing HPC was stained with the following antibody set for each sample group.

TABLE 1

| sample group (antibody set) | antibody | manufacturer | fluorescent molecule bonded to antibody |
|---|---|---|---|
| 1 | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD62L antibody | Biolegend | PE |
| 2 | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD24 antibody | Biolegend | PE |
| 3 | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD90 antibody | Biolegend | PE |
| 4 | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD143 antibody | Biolegend | PE |
| 5 | anti-CD34 antibody | Abcam | PE-Cy7 |
| | anti-CD43 antibody | BD | BV510 |
| | anti-CD45 antibody | Biolegend | APC/Cy7 |
| | anti-CD14 antibody | Biolegend | FITC |
| | anti-CD235a antibody | BD | FITC |
| | anti-CD218a antibody | eBioscience | APC |

TABLE 1-continued

| sample group (antibody set) | antibody | manufacturer | fluorescent molecule bonded to antibody |
|---|---|---|---|
| 6 | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD263 antibody | Biolegend | PE |
| 7 | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-Notch3 antibody | Biolegend | PE |

The cell populations after the above-mentioned staining were subjected to sorting by FACSAria. The cell fractions obtained from each of the above-mentioned sample groups are shown below.

TABLE 2

| sample group | obtained cell fraction |
|---|---|
| 1 | fraction A, fraction B and fraction C |
| 2 | Fraction D and fraction E |
| 3 | Fraction F and fraction G |
| 4 | Fraction H and fraction I |
| 5 | Fraction J and fraction K |
| 6 | Fraction L and fraction M |
| 7 | Fraction N and fraction O |

In the above Table, fractions A-G respectively show the following.

fraction A: CD235a negative, CD14 negative, CD34 positive, CD43 positive fraction B: CD235a negative, CD14 negative, CD34 positive, CD43 positive, CD62L positive fraction C: CD235a negative, CD14 negative, CD34 positive, CD43 positive, CD62L negative fraction D: CD235a negative, CD14 negative, CD34 positive, CD43 positive, CD24 positive fraction E: CD235a negative, CD14 negative, CD34 positive, CD43 positive, CD24 negative fraction F: CD235a negative, CD14 negative, CD34 positive, CD43 positive, CD90 positive fraction G: CD235a negative, CD14 negative, CD34 positive, CD43 positive, CD90 negative fraction H: CD235a negative, CD14 negative, CD34 positive, CD43 positive, CD143 positive fraction I: CD235a negative, CD14 negative, CD34 positive, CD43 positive, CD143 negative fraction J: CD235a negative, CD14 negative, CD34 positive, CD43 positive, CD218a positive fraction K: CD235a negative, CD14 negative, CD34 positive, CD43 positive, CD218a negative fraction L: CD235a negative, CD14 negative, CD34 positive, CD43 positive, CD263 positive fraction M: CD235a negative, CD14 negative, CD34 positive, CD43 positive, CD263 negative fraction N: CD235a negative, CD14 negative, CD34 positive, CD43 positive, Notch3 positive fraction O: CD235a negative, CD14 negative, CD34 positive, CD43 positive, Notch3 negative The cells containing in the above-mentioned fractions A-O were differentiated into lymphoid cells according to a known method (for example, the methods described in Journal of Leukocyte Biology 96(2016) 1165-1175 and WO 2017/221975). To be specific, each cell population of fractions A-O was seeded at 2000 cells/well in a 48-well-plate coated with Recombinat h-DLL4/Fc chimera (Sino Biological) and Retronectin (Takara Bio Inc.), and cultured under the conditions of 5% $CO_2$, 37° C. During the culture period, the medium was changed every 2 or 3 days. As the medium, OP9 medium (containing 15% FBS, 2 mM L-glutamine, 100 Uml penicillin, 100 ng/ml streptomycin, 55 μM 2-mercaptoethanol, 50 μg/ml ascorbic acid, 10 ng/ml human insulin, 5.5 μg/ml human transferrin, 5 ng/ml sodium selenite) added with 50 ng/ml SCF, 50 ng/ml IL-7, 50 ng/ml Flt3L, 100 ng/ml TPO, 15 μM SB203580, 30 ng/ml SDF-1α was used. On day 7 and day 14 from the start of culturing, the cells were passaged in a 48-so well-plate with similar coating. All cells were recovered on day 21 from the start of culturing, counted using a hemocytometer and stained using the following antibody set.

TABLE 3

| Antibody set | manufacturer | fluorescence molecule bonded to antibody |
|---|---|---|
| anti-CD3 antibody | Biolegend | APC/Cy7 |
| anti-CD45 antibody | Biolegend | Brilliant Violet 510 |
| anti-TCRab antibody | eBioscience | FITC |
| anti-CD8b antibody | Beckman | PE |
| anti-CD7 antibody | Biolegend | APC |
| anti-CD5 antibody | eBioscience | PE/Cy7 |
| anti-CD8a antibody | Biolegend | PerCP/Cy5.5 |
| anti-CD4 antibody | Biolegend | BV421 |

The cell populations after the above-mentioned staining were subjected to sorting by FACSAria. The cell fractions obtained by the above-mentioned sorting are shown below. In the present description, the lymphocyte fraction refers to a fraction separated using FSC (forward scatter) and SSC (side scatter) as indices in the same manner as in the method described in Cytometry (Communications in Clinical Cytometry) 18 (1994) 199-208.

fraction P: lymphocyte fraction fraction Q: lymphocyte fraction, CD3 positive, CD45 positive, CD5 positive, CD7 positive fraction R: lymphocyte fraction, CD3 positive, CD45 positive, CD7 positive, CD8a positive, CD4 positive fraction S: lymphocyte fraction, CD3 positive, CD45 positive, CD7 positive, CD8a positive, CD4 negative The number of cells of each sample derived from fractions A-O on day 21 from the start of culture (ratio to the number of cells of sample derived from fraction A) is shown in Table 4.

From Table 4, it was found that the cell populations contained in the samples derived from fraction B (CD62L positive), fraction D (CD24 positive), fraction F (CD90 positive), fraction H (CD143 positive), fraction J (CD218a positive), fraction L (CD263 positive) and fraction N (Notch3 positive) are superior in the proliferation potency as compared to the cell population contained in the sample derived from fraction A.

The number of cells of cell fractions P—S obtained by sorting by FACSAria on day 21 of culture (ratio to the number of cells of sample derived from fraction A) is shown in Table 5.

TABLE 5

| | Fraction P | Fraction Q | Fraction R | Fraction S |
|---|---|---|---|---|
| derived from Fraction A | 1 | 1 | 1 | 1 |
| derived from Fraction F | 4.2-7.9 | 19-62 | 26-222 | 23-69 |
| derived from Fraction H | 6.4-9.2 | 42-83 | 143-458 | 46-67 |
| derived from Fraction J | 6.1-7.9 | 31-50 | 191-455 | 20-28 |

As a result, it was shown that a cell population containing (a) CD3 positive, CD45 positive, CD5 positive, CD7 positive, CD8a positive, and CD4 positive cells or (b) CD3 positive, CD45 positive, CD5 positive, CD7 positive, CD8a positive, and CD4 negative cells at a high ratio can be prepared using the cells derived from fraction F, as compared to the use of cells derived from fraction G or fraction A. Similarly, it was shown that a cell population containing a high proportion of (a) CD3 positive, CD45 positive, CD5 positive, CD7 positive, CD8a positive, and CD4 positive cells, or (b) a cell population containing a high proportion of CD3 positive, CD45 positive, CD5 positive, CD7 positive, CD8a positive, and CD4 negative cells can be prepared by using cells derived from fraction H. Also, it was shown that a cell population containing CD3 positive CD45 positive CD5 positive CD7 positive CD8a positive CD4 positive cell or CD3 positive CD45 positive CD5 positive CD7 positive CD8a positive CD4 negative cell at a high ratio can be prepared using the cells derived from fraction J, as compared to the use of cells derived from fraction K or fraction A. That is, it was shown that a cell population containing CD4/CD8 double positive cell (or CD8 positive cell) at a high ratio can be prepared by separating cells expressing CD90, CD143 or CD218a as a cell population containing hematopoietic progenitor cells and differentiating the separated cells.

Example 2 ((Consideration Using Ff-I01s04 Strain)

As a cell population containing hematopoietic progenitor cells (hereinafter sometimes referred to as HPC), a non-

TABLE 4

| Fraction A | Fraction B | Fraction C | Fraction D | Fraction E | Fraction F | Fraction G | Fraction H | Fraction I | Fraction J | Fraction K | Fraction L | Fraction M | Fraction N | Fraction O |
|---|---|---|---|---|---|---|---|---|---|---|---|---|---|---|
| 1 | 6.1 | 0.9 | 4.9 | 1 | 2.4 | 0.5 | 5.8 | 1 | 9.4 | 1.6 | 5.9 | 0.6 | 14 | 0.8 |

adherent cell population obtained by differentiation of iPS cells (Ff-I01s04 strain) according to the methods described in Example 1 was used.

The cell population containing HPC was stained with an antibody set 3, 4, 5 or 6 for each sample group shown in Example 1 (respectively indicated as 3b, 4b, 5b, 6b in this Example) or antibody set 8b shown below.

TABLE 6

| sample group (antibody set) | antibody | manufacturer | fluorescence molecule bonded to antibody |
|---|---|---|---|
| 3b | anti-CD34 antibody | Abcam | PE/Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD90 antibody | Biolegend | PE |
| 8b | anti-CD34 antibody | Abcam | PE/Cy7 |
| | anti-CD43 antibody | BD | BV510 |
| | anti-CD45 antibody | Biolegend | APC/Cy7 |
| | anti-CD14 antibody | Biolegend | FITC |
| | anti-CD235a antibody | BD | FITC |
| | anti-CD200 antibody | Biolegend | Brilliant Violet 421 |
| 4b | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD143 antibody | Biolegend | PE |
| 5b | anti-CD34 antibody | Abcam | PE-Cy7 |
| | anti-CD43 antibody | BD | BV510 |
| | anti-CD45 antibody | Biolegend | APC/Cy7 |
| | anti-CD14 antibody | Biolegend | FITC |
| | anti-CD235a antibody | BD | FITC |
| | anti-CD218a antibody | eBioscience | APC |
| 6b | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD263 antibody | Biolegend | PE |

The cell populations after the above-mentioned staining were subjected to sorting by FACSAria. The cell fractions obtained from each of the above-mentioned sample groups are shown below.

TABLE 7

| sample group | obtained cell fraction |
|---|---|
| 3b | Fraction f and fraction g |
| 8b | Fraction t and fraction u |
| 4b | Fraction h and fraction i |
| 5b | Fraction j and fraction k |
| 6b | Fraction l and fraction m |

In the above Table, fractions f-m, t and u respectively show the following.

fraction f: CD235a negative, CD14 negative, CD34 positive, CD43 positive, CD90 positive fraction g: CD235a negative, CD14 negative, CD34 positive, CD43 positive, CD90 negative fraction h: CD235a negative, CD14 negative, CD34 positive, CD43 positive, CD143 positive fraction i: CD235a negative, CD14 negative, CD34 positive, CD43 positive, CD143 negative fraction j: CD235a negative, CD14 negative, CD34 positive, CD43 positive, CD218a positive fraction k: CD235a negative, CD14 negative, CD34 positive, CD43 positive, CD218a negative fraction l: CD235a negative, CD14 negative, CD34 positive, CD43 positive, CD263 positive fraction m: CD235a negative, CD14 negative, CD34 positive, CD43 positive, CD263 negative fraction t: CD235a negative, CD14 negative, CD34 positive, CD43 positive, CD200 positive fraction u: CD235a negative, CD14 negative, CD34 positive, CD43 positive, CD200 negative The cells contained in the above-mentioned fractions f-m, t and u were differentiated into lymphoid cells according to the methods described in Example 1. All cells were recovered on day 28 from the start of culturing and stained using the following antibody set.

TABLE 8

| Antibody set | manufacturer | fluorescence molecule bonded to antibody |
|---|---|---|
| CD3 | Biolegend | APC/Cy7 |
| CD45 | Biolegend | Brilliant Violet 510 |
| TCRab | eBioscience | FITC |
| CD8b | Beckman | PE |
| CD7 | Biolegend | APC |
| CD5 | eBioscience | PE/Cy7 |
| CD8a | Biolegend | PerCP/Cy5.5 |
| CD4 | Biolegend | BV421 |

The cell populations after the above-mentioned staining were subjected to sorting by FACSAria. The cell fractions obtained by the above-mentioned sorting are shown below.

fraction p: lymphocyte fraction fraction q: lymphocyte fraction, CD45 positive, CD5 positive, CD7 positive fraction r: lymphocyte fraction, CD45 positive, CD7 positive, CD8a positive, CD4 positive fraction s: lymphocyte fraction, CD45 positive, CD7 positive, CD8a positive, CD4 negative The number of cells of each sample derived from fractions f-m, t and u on day 28 from the start of culturing (ratio to the number of cells when the culturing was started) is shown in Table 9.

TABLE 9

| Fraction f | Fraction g | Fraction h | Fraction i | Fraction j | Fraction k | Fraction l | Fraction m | Fraction t | Fraction u |
|---|---|---|---|---|---|---|---|---|---|
| 462.5 | 111.9 | 462.5 | 112.5 | 1125 | 50 | 1222.6 | 56.25 | 850 | 62.5 |

From Table 9, it was found that fraction f is superior to fraction g, fraction h is superior to fraction i, fraction j is superior to fraction k, fraction l is superior to fraction m and fraction t is superior to fraction u, each in the proliferation potency. That is, it was found that the cell populations contained in the samples derived from CD90 positive, CD143 positive, CD218a positive, CD263 positive or CD200 positive are superior in the proliferation potency.

The number of cells of cell fractions p—s obtained by sorting by FACSAria on day 28 of culturing when the cells contained in fractions f-m, t and u were seeded at 1000 cells/well is shown in Table 10.

TABLE 10

| | Fraction p | Fraction q | Fraction r | Fraction s |
|---|---|---|---|---|
| derived from Fraction f | 208125 | 139860 | 7553 | 40626 |
| derived from Fraction g | 12085 | 0 | 0 | 0 |
| derived from Fraction h | 151700 | 96801 | 18704 | 81257 |
| Fraction i derived from | 11216 | 0 | 0 | 0 |
| derived from Fraction j | 409500 | 322088 | 83093 | 228521 |
| derived from Fraction k | 4430 | 0 | 0 | 0 |
| derived from Fraction l | 419352 | 257113 | 22019 | 277591 |
| derived from Fraction m | 8325 | 2683 | 159 | 3992 |
| derived from Fraction t | 342550 | 262480 | 59781 | 125477 |
| derived from Fraction u | 2569 | 0 | 0 | 0 |

An analysis by FACS on day 28 of culture shown in Table reveals that (a) CD45 positive, CD5 positive, CD7 positive, CD8a positive, and CD4 positive cells, or (b) CD45 positive, CD5 positive, CD7 positive, CD8a positive, and CD4 negative cells can be prepared at a high ratio by using cells derived from each marker positive cell, as compared to the use of cells derived from each marker negative cell.

From these results, it was shown that a cell population containing CD8 positive cells (e.g., CD4/CD8DP cell, CD8SP cell) at a high ratio can be prepared by separating cells expressing CD90, CD143, CD200, CD218a or CD263 as a cell population containing hematopoietic progenitor cells and differentiating the separated cells.

Example 3 (Consideration Using Ff-I01s04 Strain)

As a cell population containing hematopoietic progenitor cells (hereinafter sometimes referred to as HPC), a non-adherent cell population obtained by subjecting iPS cells (Ff-I01s04 strain) to the method described in Example 1 was used. The above-mentioned non-adherent cell population containing HPC was stained with the following antibody set for each sample group.

TABLE 11-1

| sample group (antibody set) | antibody | manufacturer | fluorescence molecule bonded to antibody |
|---|---|---|---|
| 1c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD7 antibody | Biolegend | PE |
| 2c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD144 antibody | BD | BV421 |
| 3c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD56 antibody | Biolegend | PE |

TABLE 11-1-continued

| sample group (antibody set) | antibody | manufacturer | fluorescence molecule bonded to antibody |
|---|---|---|---|
| 4c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD226 antibody | Biolegend | PE |
| 5c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD262 antibody | Biolegend | PE |
| 6c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor78 0 |
| | anti-CD235a antibody | BD | FITC |
| | anti-CD325 antibody | Biolegend | PE |
| 7c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD49f antibody | Biolegend | PE |
| 8c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD51 antibody | Biolegend | PE |

TABLE 11-2

| | | | |
|---|---|---|---|
| 9c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD102 antibody | Biolegend | PE |
| 10c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD42b antibody | Biolegend | PE |
| 11c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD61 antibody | Biolegend | PE |
| 12c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD62P antibody | Biolegend | PE |
| 13c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD69 antibody | Biolegend | PE |
| 14c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD102 antibody | Biolegend | PE |

TABLE 11-2-continued

| | | | |
|---|---|---|---|
| 15c | anti-CD34 antibody | Abcam | PE-Cy7 |
| | anti-CD43 antibody | BD | APC |
| | anti-CD45 antibody | Biolegend | BV510 |
| | anti-CD14 antibody | Biolegend | APC/eFluor780 |
| | anti-CD235a antibody | BD | FITC |
| | anti-CD156c antibody | Biolegend | PE |

The cell populations after the above-mentioned staining were subjected to sorting by FACSAria. The cell fractions obtained from each of the above-mentioned sample groups are shown below.

TABLE 12

| sample group | obtained cell fraction |
|---|---|
| 1c | fraction Ac and fraction Bc |
| 2c | fraction Cc |
| 3c | fraction Dc |
| 4c | fraction Ec |
| 5c | fraction Fc |
| 6c | fraction Gc |
| 7c | fraction Hc |
| 8c | fraction Ic |
| 9c | fraction Jc |
| 10c | fraction Kc |
| 11c | fraction Lc |
| 12c | fraction Mc |
| 13c | fraction Nc |
| 14c | fraction Oc |
| 15c | fraction Pc |

In the above Table, fractions Ac-Pc respectively show the following.

fraction Ac: CD235a negative, CD14 negative, CD34 positive, CD43 positive fraction Bc: CD235a negative, CD14 negative, CD34 positive, CD43 positive, CD7 positive fraction Cc: CD235a negative, CD14 negative, CD34 positive, CD43 positive, CD144 positive fraction Dc: CD235a negative, CD14 negative, CD34 positive, CD43 positive, CD56 positive fraction Ec: CD235a negative, CD14 negative, CD34 positive, CD43 positive, CD226 positive fraction Fc: CD235a negative, CD14 negative, CD34 positive, CD43 positive, CD262 positive fraction Gc: CD235a negative, CD14 negative, CD34 positive, CD43 positive, CD325 positive fraction Hc: CD235a negative, CD14 negative, CD34 positive, CD43 positive, CD49f positive fraction Ic: CD235a negative, CD14 negative, CD34 positive, CD43 positive, CD51 positive fraction Jc: CD235a negative, CD14 negative, CD34 positive, CD43 positive, CD102 positive fraction Kc: CD235a negative, CD14 negative, CD34 positive, CD43 positive, CD42b positive fraction Lc: CD235a negative, CD14 negative, CD34 positive, CD43 positive, CD61 positive fraction Mc: CD235a negative, CD14 negative, CD34 positive, CD43 positive, CD62P positive fraction Nc: CD235a negative, CD14 negative, CD34 positive, CD43 positive, CD69 positive fraction Oc: CD235a negative, CD14 negative, CD34 positive, CD43 positive, CD102 positive fraction Pc: CD235a negative, CD14 negative, CD34 positive, CD43 positive, CD156c positive The cells contained in the above-mentioned fractions Ac-Pc were differentiated into lymphoid cells by the method described in Example 1. All cells were recovered on day 21 from the start of culturing, counted using a hemocytometer and stained using the following antibody set.

TABLE 13

| antibody set | manufacturer | fluorescence molecule bonded to antibody |
|---|---|---|
| anti-CD3 antibody | Biolegend | APC/Cy7 |
| anti-CD45 antibody | Biolegend | Brilliant Violet 510 |
| anti-TCRab antibody | eBioscience | FITC |
| anti-CD8b antibody | Beckman | PE |
| anti-CD7 antibody | Biolegend | APC |
| anti-CD5 antibody | eBioscience | PE/Cy7 |
| anti-CD8a antibody | Biolegend | PerCP/Cy5.5 |
| anti-CD4 antibody | Biolegend | BV421 |

The cell populations after the above-mentioned staining were subjected to sorting by FACSAria. The cell fractions obtained by the above-mentioned sorting are shown below.

fraction Qc: lymphocyte fraction fraction Rc: lymphocyte fraction, CD3 positive, CD45 positive, CD5 positive, CD7 positive fraction Sc: lymphocyte fraction, CD3 positive, CD45 positive, CD7 positive, CD8a positive, CD4 positive fraction Tc: lymphocyte fraction, CD3 positive, CD45 positive, CD7 positive, CD8a positive, CD4 negative The number of cells of each sample derived from fractions Ac-Pc on day 21 from the start of culturing (ratio to the number of cells of sample derived from fraction Ac) is shown in Table 14.

TABLE 14

| fraction Ac | fraction Bc | fraction Cc | fraction Dc | fraction Ec | fraction Fc |
|---|---|---|---|---|---|
| 1 | 3.1 | 3.5 | 1.2 | 2.0 | 3.9 |
| **fraction Gc** | **fraction Hc** | **fraction Ic** | **fraction Jc** | **fraction Kc** | **fraction Lc** |
| 1.8 | 0 | 0.2 | 1.0 | 0.7 | 0.5 |
| **fraction Mc** | **fraction Nc** | **fraction Oc** | **fraction Pc** | | |
| 0 | 0.1 | 1.0 | 0.2 | | |

From Table 14, it was found that all cell populations contained in the samples derived from fraction Bc (CD7 positive), fraction Cc (CD144 positive), fraction Dc (CD56 positive), fraction Ec (CD226 positive), fraction Fc (CD262 positive) and fraction Gc (CD325 positive) are superior in the proliferation potency as compared to the cell population in the sample derived from fraction Ac. In addition, it was found that the cell populations contained in the samples derived from fraction Hc (CD49f positive), fraction Ic (CD51 positive), fraction Kc (CD42b positive), fraction Lc (CD61 positive), fraction Mc (CD62P positive), fraction Nc (CD69 positive) and fraction Pc (CD156c positive) are inferior in the proliferation potency.

The number of cells of cell fractions Qc-Tc obtained by sorting by FACSAria on day 21 of culturing (ratio to the number of cells of cell fractions Qc-Tc in sample derived from fraction Ac) is shown in Table 15.

TABLE 15

| | fraction Qc | fraction Rc | fraction Sc | fraction Tc |
|---|---|---|---|---|
| derived from fraction Bc | 3.3 | 3.7 | 3.1 | 2.6 |
| derived from fraction Cc | 3.8 | 4.3 | 7.0 | 2.4 |
| derived from fraction Dc | 1.3 | 1.4 | 2.2 | 0.9 |
| derived from fraction Ec | 0.9 | 1.0 | 1.7 | 0.7 |
| derived from fraction Fc | 4.1 | 4.7 | 6.5 | 2.9 |
| derived from fraction Gc | 2.1 | 2.4 | 3.1 | 1.7 |
| derived from fraction Hc | 0 | 0 | 0 | 0 |
| derived from fraction Ic | 0.2 | 0.1 | 0 | 0.2 |
| derived from fraction Jc | 1.2 | 0.7 | 0.3 | 0.6 |
| derived from fraction Kc | 0.8 | 0.7 | 0.3 | 0.8 |
| derived from fraction Lc | 0.3 | 0.3 | 0.5 | 0.3 |
| derived from fraction Mc | 0 | 0 | 0 | 0 |
| derived from fraction Nc | 0 | 0 | 0 | 0 |
| derived from fraction Oc | 1.2 | 0.7 | 0.3 | 0.6 |
| derived from fraction Pc | 0.1 | 0.1 | 0.1 | 0.1 |

As a result, it was shown that a cell population containing CD3 positive CD45 positive CD7 positive CD8a positive CD4 positive cell, or CD3 positive CD45 positive CD7 positive CD8a positive CD4 negative cell at a high ratio can be prepared by using cells derived from fraction Bc, fraction Cc, fraction Dc, fraction Ec, fraction Fc or fraction Gc, as compared to the use of cells derived from fraction Ac. In addition, it was shown that a cell population containing CD3 positive CD45 positive CD7 positive CD8a positive CD4 positive cell, or CD3 positive CD45 positive CD7 positive CD8a positive CD4 negative cell at a low ratio can be prepared by using cells derived from fraction Hc, fraction Ic, fraction Jc, fraction Kc, fraction Lc, fraction Mc, fraction Nc, fraction Oc or fraction Pc, as compared to the use of cells derived from fraction Ac. That is, it was shown that a cell population containing CD4/CD8 double positive cells (or CD8 single positive cell) at a high ratio can be prepared by separating a cell expressing any one or more kinds of CD7, CD144, CD56, CD226, CD262 and CD325, or a cell not expressing any one or more kinds of CD49f, CD51, CD102, CD42b, CD61, CD62P, CD69, CD102 and CD156c as a cell population containing hematopoietic progenitor cells and differentiating the separated cells.

This application is based on a patent application No. 2017-087723 filed in Japan (filing date: Apr. 26, 2017), the contents of which are incorporated in full herein.

INDUSTRIAL APPLICABILITY

The present invention can provide more immature T cells and mature T cells and/or provide them at higher concentrations. The thus-obtained cells are useful for the prophylaxis or treatment of diseases such as tumor, infection, autoimmune disorder and the like.

The invention claimed is:

1. A method for producing CD4/CD8 double positive cells, the method comprising (i) inducing differentiation of a population of human induced pluripotent stem cells to obtain a cell population comprising hematopoietic progenitor cells (a) expressing CD34, CD218a and CD43, and (b) not expressing CD235a and CD14, (ii) isolating hematopoietic progenitor cells expressing CD34, CD218a and CD43, and (ii) not expressing CD235a and CD14 from the cell population comprising hematopoietic progenitor cells obtained from step (i), and (iii) differentiating the isolated hematopoietic progenitor cells from step (ii) into CD4/CD8 double positive cells.

2. A method for producing CD8 single positive cells, the method comprising (i) inducing differentiation of a population of human induced pluripotent stem cells to obtain a cell population comprising hematopoietic progenitor cells (a) expressing CD34, CD218a and CD43, and (b) not expressing CD235a and CD14, (ii) isolating hematopoietic progenitor cells expressing CD34, CD218a and CD43, and (ii) not expressing CD235a and CD14 from the cell population comprising hematopoietic progenitor cells obtained from step (i), and (iii) differentiating the isolated hematopoietic progenitor cells from step (ii) into CD4/CD8 double positive cells, and (iv) inducing the CD4/CD8 double positive cells from step (iii) into single positive CD8 cells.

3. The method according to claim 2, wherein said CD8 single positive cells are cytotoxic T lymphocytes.

* * * * *